US009255059B2

(12) United States Patent
Weakley et al.

(10) Patent No.: US 9,255,059 B2
(45) Date of Patent: Feb. 9, 2016

(54) METHOD FOR PRODUCING AN ALKYL 3-HYDROXYBUTYRATE

(71) Applicant: Eastman Chemical Company, Kingsport, TN (US)

(72) Inventors: Garry Kenneth Weakley, Kingsport, TN (US); Charles Everette Kelly, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 13/957,642

(22) Filed: Aug. 2, 2013

(65) Prior Publication Data

US 2015/0038734 A1 Feb. 5, 2015

(51) Int. Cl.
*C07C 67/31* (2006.01)
*C07C 67/46* (2006.01)

(52) U.S. Cl.
CPC ............... *C07C 67/31* (2013.01); *C07C 67/46* (2013.01)

(58) Field of Classification Search
CPC .......... C07C 67/46; C07C 67/54; C07C 67/31
See application file for complete search history.

(56) References Cited

U.S. PATENT DOCUMENTS

| | | | |
|---|---|---|---|
| 2,351,366 A | 6/1944 | Pohl et al. | |
| 2,396,278 A | 3/1946 | Lind | |
| 2,486,921 A | 11/1949 | Byerly | |
| 2,486,922 A | 11/1949 | Strain | |
| 2,847,423 A | 8/1958 | Lacey | |
| 3,332,880 A | 7/1967 | Kessler et al. | |
| 3,513,189 A | 5/1970 | Marcus | |
| 4,005,189 A | 1/1977 | Reese et al. | |
| 4,994,602 A | 2/1991 | Seido et al. | |
| 5,183,929 A | 2/1993 | Naito et al. | |
| 5,420,335 A | 5/1995 | Birkhahn et al. | |
| 5,508,435 A | 4/1996 | Armstrong, III et al. | |
| 5,519,161 A | 5/1996 | Birkhahn et al. | |
| 5,612,303 A | 3/1997 | Takayanagi et al. | |
| 5,686,489 A | 11/1997 | Yu et al. | |
| 5,693,850 A * | 12/1997 | Birkhahn et al. | 560/189 |
| 5,800,897 A | 9/1998 | Sharma et al. | |
| 5,876,621 A | 3/1999 | Sapienza | |
| 5,980,774 A | 11/1999 | Sapienza | |
| 6,043,063 A | 3/2000 | Kurdikar et al. | |
| 6,075,154 A | 6/2000 | Gonda et al. | |
| 6,083,729 A | 7/2000 | Martin et al. | |
| 6,307,094 B1 | 10/2001 | Chong et al. | |
| 6,492,545 B2 | 12/2002 | Saito et al. | |
| 6,586,152 B1 | 7/2003 | Urano et al. | |
| 6,709,848 B1 | 3/2004 | Martin et al. | |
| 6,818,789 B2 | 11/2004 | Fleming et al. | |
| 6,843,931 B2 | 1/2005 | Sapienza | |
| 6,844,447 B2 | 1/2005 | Zhong et al. | |
| 6,897,338 B2 | 5/2005 | Zhong et al. | |
| 6,933,404 B2 | 8/2005 | Zhong et al. | |
| 6,939,981 B1 | 9/2005 | Boaz | |
| 7,001,969 B2 | 2/2006 | Zhong et al. | |
| 7,057,064 B2 | 6/2006 | Proctor et al. | |
| 7,166,743 B2 | 1/2007 | Zhong et al. | |
| 7,230,144 B2 | 6/2007 | Zhong et al. | |
| 7,419,759 B2 | 9/2008 | Kim et al. | |
| 7,485,452 B2 | 2/2009 | Hwang et al. | |
| 7,563,385 B2 | 7/2009 | Sapienza | |
| 7,795,376 B2 | 9/2010 | Van Walsem et al. | |
| 8,338,145 B2 | 12/2012 | Tsobanakis et al. | |
| 8,642,654 B2 | 2/2014 | Clarke et al. | |
| 2005/0221457 A1 | 10/2005 | Tsobanakis et al. | |
| 2006/0078596 A1 | 4/2006 | Clarke et al. | |
| 2006/0251597 A1 | 11/2006 | Van Scott et al. | |
| 2007/0082832 A1 | 4/2007 | DiCosimo et al. | |
| 2007/0208183 A1 | 9/2007 | Haan et al. | |
| 2008/0038802 A1 | 2/2008 | Hwang et al. | |
| 2008/0287538 A1 | 11/2008 | Scholz et al. | |
| 2009/0298144 A1 | 12/2009 | Tsobanakis et al. | |
| 2010/0119939 A1 | 5/2010 | Misumi et al. | |
| 2010/0286017 A1 | 11/2010 | Righetto | |
| 2011/0101268 A1 | 5/2011 | Choi et al. | |
| 2011/0107660 A1 | 5/2011 | Chen et al. | |
| 2011/0151379 A1 | 6/2011 | Choi et al. | |
| 2011/0195839 A1 | 8/2011 | Schlotterbeck et al. | |
| 2011/0195846 A1 | 8/2011 | Troppmann et al. | |

(Continued)

FOREIGN PATENT DOCUMENTS

EP 1502584 A1 2/2005
EP 1537247 B1 9/2007

(Continued)

OTHER PUBLICATIONS

Klabunovskii et al, Reaction Kinetics and Catalysis Letters, On the Asymmetrizing and Catalytic Activity of Ru Catalysts, 1975,vol. 2, No. 3, pp. 921-926.*
Laird, Chemical Industry Digest, How to Minimize Scale Up Difficulties, Jul. 2010, pp. 51-56.*
Wrightson et al, www.rsc.org, Safety Issues in the Scale-Up of Chemical Reactions, 2013, pp. 1-6.*
ASTM D1160.
ASTM D7236-07.
ASTM E659-78.
ASTM D4052-11.
ASTM D4488.
Vuitel et al., "Etude de la reactivite de la function carbonyle avec le cetene en presence d'un alcoxyde de thane", Helvetica Chemica Acta, vol. 57, pp. 1713-1718 (1974).

(Continued)

*Primary Examiner* — Paul A Zucker
(74) *Attorney, Agent, or Firm* — Hovey Williams LLP

(57) ABSTRACT

A method for making an alkyl 3-hydroxybutyrate is provided. The method can include reacting an alkyl alcohol with diketene to form an alkyl acetoacetate and then hydrogenating the alkyl acetoacetate to form the alkyl 3-hydroxybutyrate. The method of the present invention may also include separating one or more impurities an alkyl acetoacetate stream and subjecting the purified acetoacetate mixture to hydrogenation to form the alkyl 3-hydroxybutyrate. Methods of the present invention can be carried out on a lab, pilot, or commercial scale.

48 Claims, 1 Drawing Sheet

(56) References Cited

U.S. PATENT DOCUMENTS

| | | |
|---|---|---|
| 2012/0064611 A1 | 3/2012 | Robertson et al. |
| 2012/0317736 A1 | 12/2012 | Gonzales et al. |
| 2013/0102663 A1 | 4/2013 | Clarke |
| 2014/0194509 A1 | 7/2014 | Clarke et al. |
| 2014/0308719 A1 | 10/2014 | Clarke et al. |
| 2015/0065571 A1 | 3/2015 | Clarke et al. |

FOREIGN PATENT DOCUMENTS

| | | |
|---|---|---|
| EP | 1601737 B1 | 10/2007 |
| FR | 2 577 922 A1 | 8/1986 |
| GB | 2511941 A | 9/2014 |
| JP | 2009-173880 A | 8/2009 |
| KR | 2006024550 A | 3/2006 |
| WO | 2011/039661 A2 | 4/2011 |
| WO | 2012/039516 A1 | 3/2012 |
| WO | WO 2014/139599 A1 | 9/2014 |

OTHER PUBLICATIONS

Riis et al., "Gas chromatograph determination of poly-β-hydroxybutyric acid in microbial biomass after hydrochloric acid propanolysis", Journal of Chromatography, vol. 445, pp. 285-289 (1988).

Adkins, et al., "The Hydrogenation of Acetoacetic Ester and Certain of its Derivatives Over Nickel", J. Am. Chem. Soc., vol. 52, pp. 5192-5198 (1930).

Co-pending U.S. Appl. No. 13/957,657 dated Aug. 2, 2013.

Co-pending U.S. Appl. No. 13/957,616 dated Aug. 2, 2013.

Co-pending U.S. Appl. No. 13/957,631 dated Aug. 2, 2013.

Notification of Transmittal of the International Search Report and the Written Opinion of the International Searching Authority with Date of Mailing Oct. 15, 2014 for International Application No. PCT/US2014/047528.

Wanfang Li, et al.; "Ru-Catalyzed Asymmetric Hydrogenation of 3-Oxoglutaric Acid Derivatives via Solvent-Assisted Pinpoint Recognition of Carbonyls in Close Chemical Propinquity"; Organic Letters, 2011, vol. 13, No. 15, 3876-3879.

Sven-Olov Lawesson et al.; "t-Butyl Acetoacetate"; Organic Syntheses, Coll. vol. 5, p. 155 (1973); vol. 42, p. 28 (1962).

USPTO Office Action dated Nov. 7, 2014 for co-pending U.S. Appl. No. 13/957,616.

Notice of Allowance for related U.S. Appl. No. 13/957,616, filed Aug. 2, 2013, dated Mar. 11, 2015, 7 pages.

Final Office Action dated Aug. 25, 2015 in related U.S. Appl. No. 13/957,631, filed Aug. 2, 2013, 12 pages.

Advisory Action dated Sep. 1, 2015 in related U.S. Appl. No. 13/957,631, filed Aug. 2, 2013, 4 pages.

Lusty, C.J. et al., Poly-β-Hydroxybutyrate Depolymerases of Pseudomonas Lemoignei, Department of Bacteriology and Immunology, University of California, Berkeley, vol. 56, Jul. 12, 1966, pp. 960-965.

Notification of Transmittal of the International Search Report and the Written Opinion of the International Searching Authority with Date of Mailing Dec. 3, 2014 for International Application No. PCT/US2014/047531.

Notification of Transmittal of the International Search Report and the Written Opinion of the International Searching Authority with Date of Mailing Dec. 3, 2014 for International Application No. PCT/US2014/047524.

Notification of Transmittal of the International Search Report and the Written Opinion of the International Searching Authority with Date of Mailing Dec. 3, 2014 for International Application No. PCT/US2014/047526.

Notice of Allowance dated May 11, 2015 for co-pending U.S. Appl. No. 13/957,616, 8 pages.

Notice of Allowance dated Jun. 8, 2015 for co-pending U.S. Appl. No. 13/957,616, 7 pages.

Office Action dated Feb. 12, 2015 for co-pending U.S. Appl. No. 13/957,631, 10 pages.

Notice of Allowance dated Jun. 26, 2015 for related U.S. Appl. No. 13/957,616, filed Aug. 2, 2013, 8 pages.

Office Action dated Jul. 13, 2015 for related U.S. Appl. No. 14/694,696; 9 pages.

* cited by examiner

METHOD FOR PRODUCING AN ALKYL 3-HYDROXYBUTYRATE

FIELD OF THE INVENTION

This invention relates to methods of making alkyl esters. More specifically, this invention relates to methods of making alkyl hydroxybutyrates.

BACKGROUND

Alkyl esters, and in particular, alkyl hydroxybutyrates may be useful in a variety of end-use applications. For example, alkyl hydroxybutyrates may be employed as pharmaceutical intermediates or as fragrances or other additives in a variety of consumer products. Recently, it has also been discovered that alkyl hydroxybutyrates may be useful as organic cleaning solvents and may be used to create aqueous cleaning compositions that are both highly effective and exhibit a benign environmental and toxicity profile. Currently, alkyl hydroxybutyrates are obtained by extracting polyalkylhydroxybutyrates (PHB) from plant materials or other biomass and then depolymerizing the PHB to form lower chain length hydroxybutyrate materials. This method is expensive, time consuming, and difficult to control and is nearly impossible to carry out on a large scale.

Thus, a need exists for an efficient method of producing an alkyl hydroxybutyrate, which can consistently provide high-purity product in a time- and cost-effective manner, preferably on a commercial scale.

SUMMARY

In one aspect, the present invention concerns a method for making an alkyl 3-hydroxybutyrate comprising (a) reacting an alkyl alcohol with diketene under reaction conditions sufficient to provide a first reaction mixture comprising an alkyl acetoacetate; and (b) contacting at least a portion of the first reaction mixture with hydrogen-containing gas in the presence of a catalyst under hydrogenation conditions sufficient to hydrogenate at least a portion of the alkyl acetoacetate to thereby provide a product comprising alkyl 3-hydroxybutyrate.

In another aspect, the present invention concerns a method for producing an alkyl 3-hydroxybutyrate, the method comprising (a) separating a feed stream comprising at least one alkyl acetoacetate into at least one impurities-enriched stream and at least one impurities-depleted stream; and (b) contacting at least a portion of the impurities-depleted stream with a hydrogen-containing gas in a hydrogenation zone under conditions sufficient to hydrogenate at least a portion of the alkyl acetoacetate to thereby form an alkyl 3-hydroxybutyrate.

BRIEF DESCRIPTION OF THE DRAWINGS

Various aspects of the present invention are described in detail below with reference to the attached drawing figures, wherein.

DETAILED DESCRIPTION

The present invention relates to methods for producing an alkyl 3-hydroxybutyrate. The alkyl 3-hydroxybutyrate produced according to methods of the present invention may be represented by the following formula:

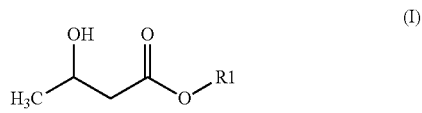

The R1 group in formula (I) above may be an alkyl group having, for example, at least 2 and not more than 8 carbon atoms. As used herein, the term "alkyl group," refers to a branched or straight-chain monovalent alkyl radical. The alkyl group may include at least 2 and not more than 7 carbon atoms, at least 3 and not more than 6 carbon atoms, at least 3 and not more than 5 carbon atoms, 3 or 4 carbon atoms, or may include 4 carbon atoms. The alkyl group group may be selected from the group consisting of isopropyl, n-propyl, isobutyl, n-butyl, 2-butyl (sec-butyl), 2,2-dimethylethyl (tert-butyl), 3,3-dimethylpentyl (isopentyl), 1-pentyl (n-pentyl), 1-methylbutyl(2-pentyl), 2-methylbutyl, 2-ethylpropyl(3-pentyl), 1,1-dimethylpropyl, 1,2-dimethylpropyl, 2,2-dimethylpropyl (neopentyl), and cyclopentyl, or may be selected from the group consisting of isopropyl, n-propyl, isobutyl, n-butyl, and 2-butyl. In some cases, the alkyl group R1 may be selected from the group consisting of isopropyl, isobutyl, n-butyl, and 2-butyl or the group consisting of isobutyl, n-butyl, and 2-butyl. Also, the R1 group can be n-butyl. The R1 group may be non-halogenated.

Figure 1:
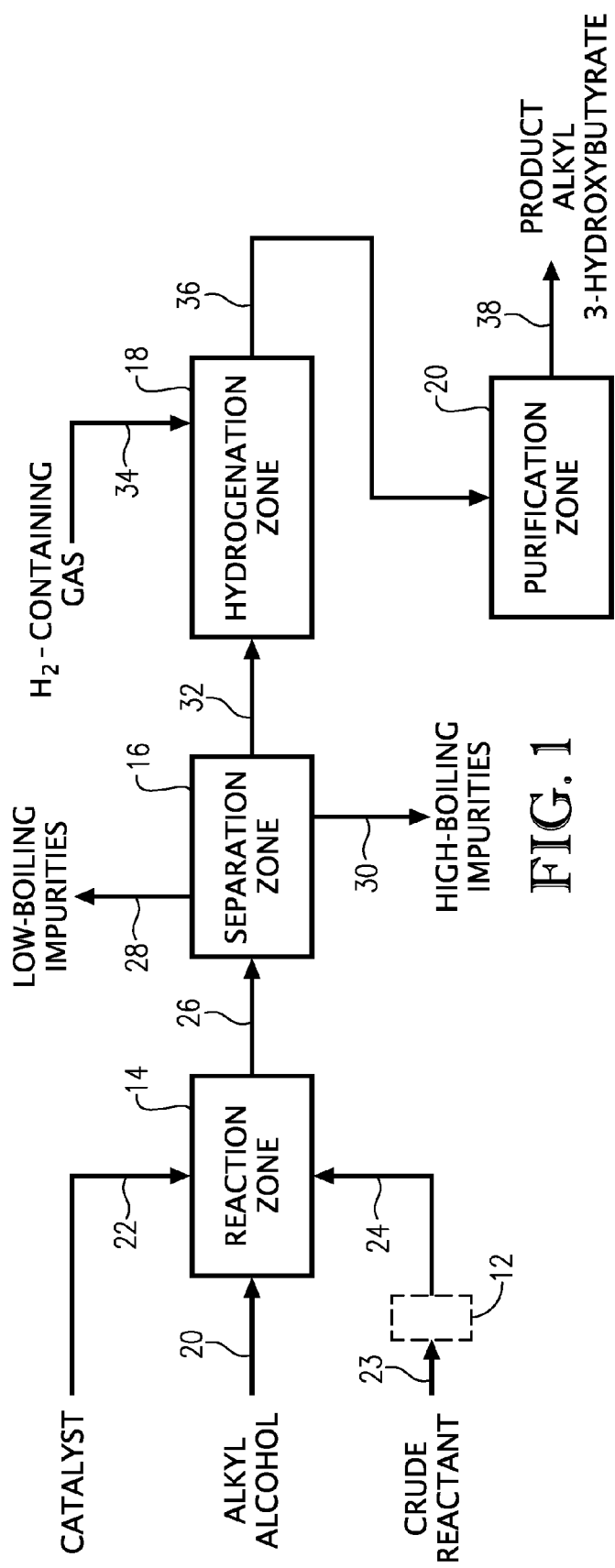
FIG. 1 is a schematic flow diagram of a production facility configured to produce alkyl 3-hydroxybutyrate.

Referring initially to FIG. 1, a schematic representation of an alkyl 3-hydroxybutyrate production facility 10 configured to illustrate one or more aspects of the present invention is provided. As represented by FIG. 1, the inventive method can include the steps of introducing an alkyl alcohol, shown by line 20, into a reaction zone 14, along with diketene, shown in line 24, and a catalyst, shown in line 22. In reaction zone 14, the alcohol can react with diketene under conditions sufficient to provide a reaction mixture comprising an alkyl acetoacetate, shown in line 26. Optionally, at least a portion of the reaction mixture in line 26 may be subjected to one or more purification steps in a separation zone 16 to remove at least one impurity before being introduced into hydrogenation zone 18, shown by line 32. In hydrogenation zone 18, the reaction mixture can be contacted with a hydrogen-containing gas in the presence of a catalyst under conditions sufficient to hydrogenate at least a portion of the alkyl acetoacetate to thereby provide a product comprising an alkyl 3-hydroxybutyrate, shown by line 36. Optionally, the product may be subjected to a post-hydrogenation purification step shown by purification zone 20 before being removed from facility 10 as a final alkyl 3-hydroxybutyrate product.

The method of the present invention may be carried out in a batch or the process may be performed in a semi-batch manner such that one or more of the process steps can be performed continuously. Alternatively, the entire process represented by facility 10 may be carried out continuously. The method represented by facility 10 may be carried out on any suitable scale and can, for example, be a laboratory- or pilot-scale facility. In other cases, the method represented by facility 10 could be carried out on a larger, commercial scale, such as, for example, in a facility having an average daily production rate, measured over a one month period, of at least about 1,000 pounds, at least about 5,000 pounds, at least about 10,000 pounds, at least about 20,000 pounds, at least about 50,000 pounds, at least about 75,000 pounds, at least about 100,000 pounds of alkyl 3-hydroxybutyrate product per day.

Referring back reaction zone 14, the alkyl alcohol introduced into reaction zone 14 via line 20 can be any suitable alkyl alcohol capable of reacting with diketene to form the desired alkyl acetoacetate. The alkyl group of the alcohol can include at least 2 and not more than 8 carbon atoms, at least 2 and not more than 7 carbon atoms, at least 3 and not more than 6 carbon atoms, at least 3 and not more than 5 carbon atoms, 3 or 4 carbon atoms, or may include 4 carbon atoms. The alkyl group may be selected from the group consisting of isopropyl, n-propyl, isobutyl, n-butyl, 2-butyl (sec-butyl), isopentyl, pentyl, and 2,2-dimethylpropyl, or may be selected from the group consisting of isopropyl, n-propyl, isobutyl, n-butyl, and 2-butyl. The alkyl group of the alcohol may be selected from the group consisting of isopropyl, isobutyl, n-butyl, and 2-butyl or the group consisting of isobutyl, n-butyl, and 2-butyl. The alkyl group of the alcohol may be n-butyl. The alkyl group of the alcohol, the acetoacetate, and the 3-hydroxybutyrate can be the same.

The diketene introduced into reaction zone 14 via line 24 may originate from any source and can optionally be purified in upstream purification zone 12 to remove at least a portion of one or more impurities from a crude diketene stream in line 23. As used herein, the term "impurity" refers to any component other than the component or components desired to be produced or used within a process or step. Examples of impurities removed from the diketene in upstream purification zone 12 may include, for example, acetone, acetic anhydride, acetic acid, and combinations thereof. Upstream purification zone 12 may be configured to remove at least about 10 percent, at least about 20 percent, at least about 30 percent, at least about 40 percent, at least about 50 percent, at least about 60 percent, at least about 70 percent, at least about 80 percent, at least about 90 percent, or at least about 95 percent of the total amount of the one or more impurities from the crude diketene stream, based on the total amount of the impurities introduced into upstream purification zone 12 via line 23.

Any suitable type of separation equipment may be used to achieve the desired degree of impurity removal from the diketene stream, including, for example, one or more distillation columns. Once purified, the diketene in line 24 may comprise not more than about 5 weight percent, not more than about 2 weight percent, not more than about 1 weight percent, not more than about 0.5 weight percent, or not more than about 0.1 weight percent of one or more impurities, based on the total weight of the purified diketene stream. Optionally, at least a portion of the crude diketene in line 23 may bypass upstream separation zone 12 and be introduced directly into reaction zone 14 (not shown in FIG. 1).

As shown in FIG. 1, the alcohol and diketene may be separately introduced into reaction zone 14. During the addition of diketene, the temperature of the reaction mixture within reaction zone 14 can be maintained at a target temperature of at least about 60° C., at least about 65° C., at least about 70° C. and/or not more than 105° C., not more than about 100° C., not more than about 95° C., or at a target temperature in the range of from about 60 to about 105° C., about 60 to about 100° C., about 60 to about 95° C., about 65 to about 105° C., about 65 to about 100° C., about 65 to about 95° C., about 70 to about 105° C., about 70 to about 100° C., about 70 to about 95° C. Preferably, the temperature of the reaction mixture can deviate from the target temperature by not more than 5°, not more than 3°, not more than about 2°, or not more than about 1° during the addition of diketene.

The alcohol may be present in the reaction mixture in a slight stoichiometric excess, based on the amount of diketene introduced into reaction zone 14. For example, the alcohol may be introduced into reaction zone 14 to achieve a slight stoichiometric excess of at least about a 1 percent, at least about a 2 percent, at least about a 5 percent stoichiometric excess, based on the total amount of diketene. The molar ratio of alcohol to diketene introduced into reaction zone 14 may be at least about 1:1.2, at least about 1:1.1, at least about 1.1 and/or not more than about 1.5:1, not more than about 1.2:1, not more than 1.1:1 or in the range of from about 1:1.2 to about 1.5:1, about 1:1.2 to about 1.2:1, about 1:1.2 to about 1.1:1, about 1:1.1 to about 1.5:1, about 1:1.1 to about 1.2:1, about 1:1.1 to about 1.1:1, about 1:1 to about 1.5:1, about 1:1 to about 1.2:1, about 1:1 to about 1.1:1.

The catalyst introduced into reaction zone 14 via line 22 may be a homogenous catalyst that is at least partially dissolvable in the reaction medium. The catalyst may be present in the reaction mixture as a solid, a liquid, or a gas, with a liquid catalyst being preferred. Desirably, the vapor pressure of the catalyst may be such that the catalyst can be contained within the reaction vessel and/or medium during the reaction and, in some cases, may be at least about 45 torr, at least about 50 torr, at least about 55 torr and/or not more than about 75 torr, not more than about 70 torr, not more than about 65 torr, measured at 25° C., or can be in the range of from about 45 to about 75 torr, about 45 to about 70 torr, about 45 to about 65 torr, about 50 to about 75 torr, about 50 to about 70 torr, about 50 to about 65 torr, about 55 to about 75 torr, about 55 to about 70 torr, about 55 to about 65 torr, measured at 25° C.

Examples of suitable catalysts can include, but are not limited to, sodium hydroxide, a sodium alkoxide, hydrogen chloride, sulfuric acid, tertiary amines, and combinations thereof. Exemplary tertiary amines can include trialkyl amines and, in particular, can include triethylamine. The catalyst can be present in reaction zone 14 in an amount of at least about 0.1 weight percent, at least about 1 weight percent, at least about 2 weight percent, at least about 3 weight percent and/or not more than about 10 weight percent, not more than about 8 weight percent, not more than about 6 weight percent, based on the total weight of the reaction mixture within reaction zone 14. The catalyst can be present in an amount in the range of from about 0.1 to about 10 weight percent, about 0.1 to about 8 weight percent, about 0.1 to about 6 weight percent, about 1 to about 10 weight percent, about 1 to about 8 weight percent, about 1 to about 6 weight percent, about 2 to about 10 weight percent, about 2 to about 8 weight percent, about 2 to about 6 weight percent, about 3 to about 10 weight percent, about 3 to about 8 weight percent, about 3 to about 6 weight percent, based on the total weight of the reaction mixture in reaction zone 14.

The diketene, alcohol, and catalyst may be introduced into reaction zone 14 in any suitable order. Two or more of the components may be combined to form a precursor mixture and the remaining component may be added to the precursor mixture within reaction zone 14. For example, the catalyst and alcohol may be combined prior to (not shown) or within reaction zone 14 to form a precursor reaction mixture. Subsequently, the diketene may be introduced in a manner described previously to maintain a target temperature within reaction zone 14. Alternatively, each of the diketene, alcohol, and catalyst may be introduced into reaction zone 14 simultaneously, with little or no mixing prior to combination.

Within reaction zone 14, the diketene and alcohol can be reacted under conditions sufficient to form a reaction mixture comprising an alkyl acetoacetate. The reaction conditions within reaction zone 14 may include a reaction temperature of at least about 55° C., at least about 60° C., at least about 65° C., at least about 70° C. and/or not more than about 105° C., not more than about 100° C., not more than about 95° C., not more than about 90° C., or in the range of from about 55 to about 105° C., about 55 to about 100° C., about 55 to about 95° C., about 55 to about 90° C., about 60 to about 105° C., about 60 to about 100° C., about 60 to about 95° C., about 60 to about 90° C., about 65 to about 105° C., about 65 to about 100° C., about 65 to about 95° C., about 65 to about 90° C., about 70 to about 105° C., about 70 to about 100° C., about 70 to about 95° C., about 70 to about 90° C. The reaction conditions may also include a reaction pressure of at least about 13 psia, at least about 14 psia, at least about 15 psia and/or not more than about 25 psia, not more than about 20 psia, or not more than about 17 psia, or in the range of from about 13 to about 25 psia, about 13 to about 20 psia, about 13 to about 17 psia, about 14 to about 25 psia, about 14 to about 20 psia, about 14 to about 17 psia, about 15 to about 25 psia, about 15 to about 20 psia, about 15 to about 17 psia. The reaction pressure may be within about 10 psi, about 5 psi, or about 2 psi of atmospheric pressure.

The reaction conditions within reaction zone 14 can also include a total reaction time of at least about 30 minutes, at least about 1 hour, at least about 2 hours and/or not more than about 8 hours, not more than about 6 hours, not more than about 4 hours. The reaction time or average residence time may be in the range of from about 30 minutes to about 8 hours, about 30 minutes to about 6 hours, about 30 minutes to about 4 hours, about 1 to about 8 hours, about 1 to about 6 hours, about 1 to about 4 hours, about 2 to about 8 hours, about 2 to about 6 hours, about 2 to about 4 hours. The actual yield of alkyl acetoacetate obtained within reaction zone 14 may be at least about 50 percent, at least about 60 percent, at least about 70 percent, at least about 80 percent, at least about 85 percent, at least about 90 percent, at least about 95 percent, as compared to the theoretical yield. The resulting reaction mixture in line 26 can comprise at least about 50 weight percent, at least about 65 weight percent, at least about 75 weight percent, at least about 80 weight percent, at least about 85 weight percent, at least about 90 weight percent alkyl acetoacetate, based on the total weight of the reaction mixture.

The reaction mixture in line 26 may also include one or more impurities, including, but not limited to, an alkyl acetate, an alkyl butyrate, a dimer, trimer, and/or oligomer of the acetoacetate, as well as residual alkyl alcohol and/or catalyst. The alkyl groups of the acetate and butyrate impurities can have the same number of carbon atoms, or can be the same, as the alkyl groups of the alkyl alcohol and alkyl acetoacetate. The reaction mixture in line 26 can have a total impurities content of at least about 0.001 weight percent, at least about 0.005 weight percent, at least about 0.10 weight percent, at least about 0.5 weight percent and/or not more than about 10 weight percent, not more than about 8 weight percent, not more than about 5 weight percent, not more than about 2 weight percent, not more than about 1 weight percent, based on the total weight of the reaction mixture in line 26. The reaction mixture in line 26 can have a total impurities content in the range of from about 0.001 to about 10 weight percent, about 0.001 to about 8 weight percent, about 0.001 to about 5 weight percent, about 0.001 to about 2 weight percent, about 0.001 to about 1 weight percent, about 0.005 to about 10 weight percent, about 0.005 to about 8 weight percent, about 0.005 to about 5 weight percent, about 0.005 to about 2 weight percent, about 0.005 to about 1 weight percent, about 0.10 to about 10 weight percent, about 0.10 to about 8 weight percent, about 0.10 to about 5 weight percent, about 0.10 to about 2 weight percent, about 0.10 to about 1 weight percent, about 0.50 to about 10 weight percent, about 0.50 to about 8 weight percent, about 0.50 to about 5 weight percent, about 0.50 to about 2 weight percent, about 0.50 to about 1 weight percent, based on the total weight of the reaction mixture.

Depending, in part, on the type and/or amount of impurities present, the reaction mixture in line 26 may be subjected to a purification step, as represented by separation zone 16 in FIG. 1, before being contacted with a hydrogen-containing gas in hydrogenation zone 18. During the purification step, at least a portion of one or more impurities present in the reaction mixture in line 26 can be removed, thereby providing a purified reaction mixture comprising alkyl acetoacetate in line 32. Separation zone 16 may be configured to remove at least about 45 percent, at least about 50 percent, at least about 55 percent, at least about 60 percent, at least about 65 percent, at least about 70 percent, at least about 75 percent, at least about 80 percent, at least about 85 percent, at least about 90 percent of the total amount of impurities present in the intermediate reaction mixture introduced into separation zone 16 via line 26. As a result of the purification carried out in separation zone 16, the purified reaction mixture in line 32 may have a total impurities content of not more than about 1 weight percent, not more than about 0.75 weight percent, not more than about 0.5 weight percent, not more than about 0.1 weight percent, or not more than about 0.05 weight percent, based on the total weight of the purified reaction mixture.

Separation zone 16 can include any process capable of or apparatus configured to separate a feed stream comprising the alkyl acetoacetate into at least one impurities-enriched stream and at least one impurities-depleted stream. The impurities-depleted stream exiting separation zone 16 via line 32 can have an acetoacetate content of at least about 50 percent, at least about 70 percent, at least about 75 percent, at least about 80 percent, based on the total weight of the impurities-depleted stream and may include at least about 50 percent, at least about 65 percent, at least about 75 percent, at least about 80 percent of the total amount of acetoacetate introduced into separation zone 16 via line 26.

Figure 2:
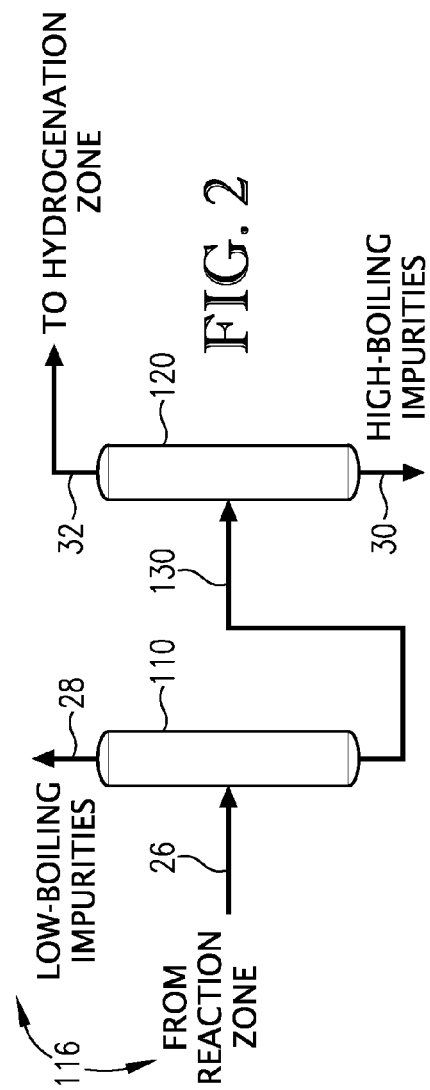
FIG. 2 is a schematic flow diagram of one example of a separation zone suitable for use in the production facility illustrated in FIG. 1.

One example of a configuration suitable for use in separation zone 16 is illustrated in FIG. 2. Separation zone 116 illustrated in FIG. 2 includes a first distillation column 110 and a second distillation column 120, arranged in series. Additional equipment, such as valves, pumps, control valves, reflux condensers, and reboilers is not shown, but can be included as appropriate and understood by one skilled in the art. As shown in FIG. 2, a feed stream in line 26, at least a portion of which may originate from reaction zone 14 in FIG. 1, may be introduced into first distillation column 110, wherein it can be separated into an overhead lights stream in line 28 and a bottoms heavies stream in line 130.

The overhead temperature of first distillation column 110 can be at least about 15° C., at least about 20° C., at least about 25° C. and/or not more than about 70° C., not more than about 65° C., not more than about 60° C., or in the range of from about 15 to about 70° C., about 15 to about 65° C., about 15 to about 60° C., about 20 to about 70° C., about 20 to about 65° C., about 20 to about 60° C., about 25 to about 70° C., about 25 to about 65° C., about 25 to about 60° C. The separating step carried out in first distillation column 110 may be performed under vacuum at a pressure of not more than about 760 torr. The overhead pressure of first distillation column 110 may be at least about 1 torr, at least about 2 torr, at least about 5 torr and/or not more than about 30 torr, not more than about 25 torr, not more than about 20 torr, or in the range of from about 1 to about 30 torr, about 1 to about 25 torr, about 1 to about 20 torr, about 2 to about 30 torr, about 2 to about 25 torr, about 2 to about 20 torr, about 5 to about 30 torr, about 5 to about 25 torr, about 5 to about 20 torr.

The overhead stream withdrawn from first distillation column 110 in line 28 may include one or more low-boiling impurities removed from the feed stream in line 26. As used herein, the term "low-boiling impurity" refers to an undesired compound or material having a boiling point lower than the compound being purified or isolated, which, in this case, may be alkyl acetoacetate. Examples of low-boiling impurities in overhead stream 28 can include, but are not limited to, acetic acid, acetone, an alkyl acetate, residual catalyst and/or residual alkyl alcohol. The alkyl acetate may have an alkyl group having the same number of carbon atoms as the alkyl group of the alkyl acetoacetate and alkyl alcohol. The alkyl groups of the alcohol, acetoacetate, and acetate impurity can be the same. The total amount of low-boiling impurities in the overhead stream in line 28 may be at least about 35 weight percent, at least about 40 weight percent, at least about 45 weight percent, at least about 50 weight percent, based on the total weight of the overhead stream. At least about 40 percent, at least about 50 percent, at least about 60 percent, at least about 70 percent, at least about 80 percent of the total amount of light-boiling impurities introduced into first distillation column 110 in feed stream 26 may be removed from feed stream 26 in first distillation column 110 via overhead stream 28.

The overhead stream in line 28 may further include at least a portion of the acetoacetate introduced into first distillation column 110. Although it may be desirable to minimize such carryover, the overhead stream in line 28 may include acetoacetate in an amount of not more than about 20 weight percent, not more than about 15 weight percent, or not more than about 10 weight percent, based on the total weight of the overhead stream. This amount of acetoacetate may be not more than about 15 percent, not more than about 10 percent, or not more than about 5 percent of the total amount of acetoacetate introduced into first distillation column 110 via the feed in line 26.

At least about 50, at least about 60, at least about 70, at least about 80, at least about 85 percent, at least about 90 percent, at least about 95 percent of the total amount of acetoacetate introduced into first distillation column 110 can be withdrawn from first distillation column 110 via the bottoms heavy stream in line 30. The ratio of the total weight of acetoacetate in the overhead stream in line 28 to the total weight of acetoacetate in the bottoms stream in line 130 can be at least about 0.01:1, at least about 0.05:1, at least about 0.10:1 and/or not more than about 0.25:1, not more than about 0.20:1, not more than about 0.15:1, or in the range of from about 0.01:1 to about 0.25:1, about 0.01:1 to about 0.20:1, about 0.01:1 to about 0.15:1, about 0.05:1 to about 0.25:1, about 0.05:1 to about 0.20:1, about 0.05:1 to about 0.15:1, about 0.10:1 to about 0.25:1, about 0.10:1 to about 0.20:1, about 0.10:1 to about 0.15:1.

The bottoms heavy stream in line 130 withdrawn from first distillation column 110 can comprise at least about 65 weight percent, at least about 70 weight percent, at least about 75 weight percent, at least about 80 weight percent, at least about 85 weight percent of the alkyl acetoacetate, based on the total weight of the bottoms stream. Additionally, the bottoms stream in line 30 can additionally include one or more impurities, such as, for example low-boiling impurities including those listed above, as well as one or more high-boiling impurities. As used herein, the term "high-boiling impurity" refers to an undesired compound or material having a boiling point higher than the material being purified or isolated, such as, for example, alkyl acetoacetate. Examples of high-boiling impurities can include, but are not limited to, dimers and trimers of the alkyl acetoacetate, alkyl butyrate, and others. The alkyl group of the alkyl butyrate may have the same number of carbon atoms as, or may be the same as, the alkyl group of the alkyl acetoacetate and alkyl alcohol. Additionally, the bottoms stream in line 130 may include one or more of the low-boiling impurities, including those listed above.

The total amount of impurities present in the bottoms stream in line 130 may be at least about 35 weight percent, at least about 40 weight percent, at least about 45 weight percent, at least about 50 weight percent, based on the total weight of the bottoms stream. At least about 70 percent, at least about 80 percent, at least about 90 percent of the total impurities in stream 130 may be high-boiling impurities, with the remaining being low-boiling impurities listed above. The bottoms stream in line 130 can have a total amount of high-boiling impurities of at least about 2 weight percent, at least about 5 weight percent, at least about 10 weight percent and/or not more than about 30 weight percent, not more than about 25 weight percent, not more than about 20 weight percent, based on the total weight of the bottoms stream in line 30. The total amount of high-boiling impurities in the bottoms stream 130 exiting first distillation column 110 can be in the range of from about 2 to about 30 weight percent, about 2 to about 25 weight percent, about 2 to about 20 weight percent, about 5 to about 30 weight percent, about 5 to about 25 weight percent, about 5 to about 20 weight percent, about 10 to about 30 weight percent, about 10 to about 25 weight percent, about 10 to about 20 weight percent, based on the total weight of the bottoms stream in line 30. At least about 40 percent, at least about 50 percent, at least about 60 percent, at least about 70 percent, at least about 80 percent of the total amount of light-boiling impurities introduced into first distillation column 110 in feed stream 26 may be removed from feed stream 26 in first distillation column 110 via overhead stream 28.

As shown in FIG. 2, the bottoms stream in line 130 can be introduced into a second distillation column 120, wherein it is separated into a second overhead lights stream in line 128 and a second bottoms heavy stream in line 126. The overhead temperature of second distillation column 120 can be at least about 70° C., at least about 75° C., at least about 80° C. and/or not more than about 90° C., not more than about 85° C., not more than about 82° C., or in the range of from about 70 to about 90° C., about 70 to about 85° C., about 70 to about 82° C., about 75 to about 90° C., about 75 to about 85° C., about 75 to about 82° C., about 80 to about 90° C., about 80 to about 85° C., about 80 to about 82° C. The separating step carried out in second distillation column 120 may be performed under vacuum at a pressure of not more than about 760 torr. The overhead pressure of second distillation column 120 may be at least about 1 torr, at least about 2 torr, at least about 5 torr and/or not more than about 30 torr, not more than about 25 torr, not more than about 15 torr, or in the range of from about 1 to about 30 torr, about 1 to about 25 torr, about 1 to about 15 torr, about 2 to about 30 torr, about 2 to about 25 torr, about 2 to about 15 torr, about 5 to about 30 torr, about 5 to about 25 torr, about 5 to about 15 torr.

The second bottoms stream in line 30 withdrawn from second distillation column 120 can be enriched in one or more high-boiling components, such as those listed previously, and may include, for example, at least about 40 percent, at least about 50 percent, at least about 60 percent, at least about 65 percent, at least about 70 percent of the total amount of high-boiling impurities introduced into second distillation column 120 via the bottoms stream from first distillation column 110 in line 30. The concentration of high-boiling impurities in the second bottoms stream in line 30 can be at least about 50 weight percent, at least about 65 weight percent, at least about 75 weight percent, or at least about 80 weight percent, based on the total weight of the second bottoms stream.

It may be possible that at least a portion of the acetoacetate introduced into second distillation column 120 may also be withdrawn via the second bottoms stream in line 30. The amount of acetoacetate removed from second distillation column 120 via the second bottoms stream 30 can be not more than about 20 percent, not more than about 15 percent, not more than about 10 percent, not more than about 5 percent of the total amount of acetoacetate introduced into second distillation column 120 via line 130. The second bottoms stream in line 30 may comprise not more than about 15 weight percent, not more than about 10 weight percent, not more than about 5 weight percent of the acetoacetate, based on the total weight of the second bottoms stream.

The second overhead stream withdrawn from second distillation column 120 in line 32 can be enriched in acetoacetate and depleted of one or more high-boiling impurities as discussed previously. The second overhead stream in line 32 can include at least about 40 percent, at least about 50 percent, at least about 60 percent, at least about 70 percent, at least about 80 percent, at least about 90 percent of the total amount of acetoacetate introduced into second distillation column 120 and comprise at least about 50 weight percent, at least about 65 weight percent, at least about 75 weight percent, at least about 80 weight percent, at least about 85 weight percent, at least about 90 weight percent of acetoacetate, based on the total weight of the stream. Additionally, the second overhead stream in line 32 may also include one or more impurities, but the total impurities content of this stream can be no more than about 15 weight percent, not more than about 10 weight percent, not more than about 5 weight percent, not more than about 2 weight percent, based on the total weight of the stream. The ratio of the total weight of acetoacetate in the second bottoms stream in line 30 to the total weight of acetoacetate in the second overhead stream in line 32 can be at least about 0.01:1, at least about 0.05:1, at least about 0.10:1 and/or not more than about 0.25:1, not more than about 0.20:1, not more than about 0.15:1, or in the range of from about 0.01:1 to about 0.25:1, about 0.01:1 to about 0.20:1, about 0.01:1 to about 0.15:1, about 0.05:1 to about 0.25:1, about 0.05:1 to about 0.20:1, about 0.05:1 to about 0.15:1, about 0.10:1 to about 0.25:1, about 0.10:1 to about 0.20:1, about 0.10:1 to about 0.15:1.

Turning back to FIG. 1, at least a portion of the purified reaction mixture in line 32, which can comprise at least a portion of the second overhead stream in line 128 withdrawn from the second distillation column 120 shown in FIG. 2, may be routed to hydrogenation zone 18 shown in FIG. 1. In hydrogenation zone 18, at least a portion of the purified reaction mixture can be contacted with a hydrogen-containing gas, introduced via line 34, in order to reduce at least a portion of the acetoacetate to produce the alkyl 3-hydroxybutyrate, as discussed in detail previously. Hydrogen-containing gas in line 34 can include at least about 50 mole percent, at least about 75 mole percent, at least about 85 mole percent, at least about 90 mole percent, at least about 95 mole percent, or at least about 97 mole percent hydrogen, based on the total moles of hydrogen-containing gas in line 34.

At least a portion of the contacting in hydrogenation zone 18 may be carried out in the presence of a hydrogenation catalyst. The catalyst can be a heterogeneous catalyst and may comprise one or more catalytic metals supported in, on, and/or within a catalyst support. The catalytic metal may be selected from the group consisting of palladium, nickel, platinum, and ruthenium and may be present in an amount of at least about 1 weight percent, at least about 2 weight percent, at least about 3 weight percent and/or not more than about 10 weight percent, not more than about 8 weight percent, not more than about 6 weight percent, or in an amount in the range of from about 1 to about 10 weight percent, about 1 to about 8 weight percent, about 1 to about 6 weight percent, about 2 to about 10 weight percent, about 2 to about 8 weight percent, about 2 to about 6 weight percent, about 3 to about 10 weight percent, about 3 to about 8 weight percent, about 3 to about 6 weight percent, based on the total weight of the catalyst. Although catalysts including more than one catalytic metal may be used, the catalyst may alternatively include only a single catalytic metal.

The catalyst support may be formed of a material selected from the group consisting of silica, alumina, aluminosilicate, and carbon. Preferably, the catalyst support may be non-acidic and does not include silica or alumina. The catalyst support may comprise or consist essentially of carbon. Catalysts and supports any suitable particle size and pore configuration may be used and the specific particle size may depend, at least in part, on the type of hydrogenation reactor employed. The hydrogenation reactor may comprise a fixed bed reactor, a fluidized bed reactor, or a hybrid thereof, with a fixed bed reactor being preferred.

The hydrogenation reaction conditions in hydrogenation zone 18 can include a temperature of at least about 60° C., at least about 65° C., at least about 70° C. and/or not more than about 100° C., not more than about 95° C., not more than about 90° C. or in the range of from about 60 to about 100° C., about 60 to about 95° C., about 60 to about 90° C., about 65 to about 100° C., about 65 to about 95° C., about 65 to about 90° C., about 70 to about 100° C., about 70 to about 95° C., about 70 to about 90° C. The hydrogenation conditions may also include a pressure of at least about 300 psig, at least about 500 psig, at least about 800 psig and/or not more than about 2000 psig, not more than about 1500 psig, not more than about 1000 psig or a pressure in the range of from about 300 to about 2000 psig, about 300 to about 1500 psig, about 300 to about 1000 psig, about 500 to about 2000 psig, about 500 to about 1500 psig, about 500 to about 1000 psig, about 800 to about 2000 psig, about 800 to about 1500 psig, about 800 to about 1000 psig. Additionally, during hydrogenation, the pH of the reaction mixture can be generally neutral and may be at least about 6, at least about 6.5, at least about 7 and/or not more than about 8, not more than about 7.5, not more than about 7.25 or in the range of from about 6 to about 8, about 6 to about 7.5, about 6 to about 7.25, about 6.5 to about 8, about 6.5 to about 7.5, about 6.5 to about 7.25, about 7 to about 8, about 7 to about 7.5, about 7 to about 7.25.

The hydrogenation may be carried out for a period of time of at least about 30 minutes, at least about 1 hour, at least about 2 hours and/or not more than about 8 hours, not more than about 6 hours, not more than about 4 hours or a period of time in the range of from about 30 minutes to about 8 hours, about 30 minutes to about 6 hours, about 30 minutes to about 4 hours, about 1 to about 8 hours, about 1 to about 6 hours, about 1 to about 4 hours, about 2 to about 8 hours, about 2 to about 6 hours, about 2 to about 4 hours. The actual yield of alkyl 3-hydroxybutyrate resulting from the hydrogenation step may be at least about 50 percent, at least about 60 percent, at least about 70 percent, at least about 80 percent, at least about 85 percent, at least about 90 percent, at least about 95 percent, as compared to theoretical. The resulting product mixture in line 36 can comprise at least about 50 weight percent, at least about 65 weight percent, at least about 75 weight percent, at least about 80 weight percent, at least about 85 weight percent, at least about 90 weight percent of the alkyl 3-hydroxybutyrate, based on the total weight of the product mixture.

The product mixture in line 36 may optionally be subjected to a post-hydrogenation purification step, as represented by purification zone 20 in FIG. 1, before being removed as a product stream in line 38. During the purification step, at least a portion of one or more residual impurities may be removed from the product mixture using, for example, one or more stages of filtration, distillation, drying, or combinations thereof. The resulting product stream in line 38 may include the product alkyl 3-hydroxybutyrate in an amount of at least about 65 weight percent, at least about 75 weight percent, at least about 80 weight percent, at least about 85 weight percent, at least about 90 weight percent, aal 95 weight percent, based on the total weight of the product stream.

The resulting alkyl 3-hydroxybutyrate may have a vapor pressure, measured via ASTM D1160 at 20° C., not more than about 0.20 torr, not more than about 0.18 torr, not more than about 0.16 torr, or not more than about 0.12 torr. In some cases, the alkyl 3-hydroxybutyrate may have a vapor pressure at 20° C. of at least about 0.05 torr, at least about 0.055 torr, at least about 0.06 torr, and/or not more than about 0.10 torr, not more than about 0.09 torr, not more than about 0.08 torr, not more than about 0.075 torr. The alkyl 3-hydroxybutyrate can have a vapor pressure, measured at 20° C., in the range of from about 0.05 to about 0.10 torr, about 0.05 to about 0.09 torr, about 0.05 to about 0.08 torr, about 0.05 to about 0.075 torr, about 0.055 to about 0.10 torr, about 0.055 to about 0.09 torr, about 0.055 to about 0.08 torr, about 0.055 to about 0.075 torr, about 0.06 to about 0.10 torr, about 0.06 to about 0.09 torr, about 0.06 to about 0.08 torr, about 0.06 to about 0.075 torr.

The alkyl 3-hydroxybutyrate can also have a boiling point, measured at atmospheric pressure using a Mettler FP81 HT MBC cell equipped with photocell detection, of at least about 150° C., at least about 200° C., at least about 210° C., at least about 215° C., at least about 216° C., or at least about 217° C. and/or not more than about 230° C., not more than about 225° C., or not more than about 220° C. The boiling point of the alkyl 3-hydroxybutyrate can be in the range of from about 150 to about 230° C., about 150 to about 225° C., about 150 to about 220° C., about 200 to about 230° C., about 200 to about 225° C., about 200 to about 220° C., about 210 to about 230° C., about 210 to about 225° C., about 210 to about 220° C., about 215 to about 230° C., about 215 to about 225° C., about 215 to about 220° C., about 216 to about 230° C., about 216 to about 225° C., about 216 to about 220° C., about 217 to about 230° C., about 217 to about 225° C., about 217 to about 220° C.

The alkyl 3-hydroxybutyrate can have a flash point, measured by ASTM D7236-07 with a Setaflash closed cup instrument, of at least about 80° C., at least about 85° C., at least about 90° C., at least about 95° C. and/or not more than about 115° C., not more than about 110° C., not more than about 105° C. and/or may have an auto-ignition temperature, measured according to ASTM E659-78 (2005), of at least about 290° C., at least about 295° C., at least about 300° C. and/or not more than about 345° C., not more than about 335° C., or not more than about 330° C. The alkyl 3-hydroxybutyrate may have a flash point in the range of from about 80 to about 115° C., about 80 to about 110° C., about 80 to about 105° C., about 85 to about 115° C., about 85 to about 110° C., about 85 to about 105° C., about 90 to about 115° C., about 90 to about 110° C., about 90 to about 105° C., from about 95 to about 115° C., about 95 to about 110° C., about 95 to about 105° C. and/or an auto-ignition temperature in the range of from about 290 to about 345° C., about 290 to about 335° C., about 290 to about 330° C., about 295 to about 345° C., about 295 to about 335° C., about 295 to about 330° C., about 300 to about 345° C., about 300 to about 335° C., about 300 to about 330° C.

The alkyl 3-hydroxybutyrate may also have a density, measured according to ASTM D4052-11 at 20° C., of at least about 0.955 g/mL, at least about 0.960 g/mL, at least about 0.965 g/mL, at least about 0.970 g/mL and/or not more than about 0.985 g/mL, not more than about 0.980 g/mL, or not more than about 0.975 g/mL. The alkyl 3-hydroxybutyrate may have a density in the range of from about 0.955 to about 0.985 g/mL, about 0.955 to about 0.980 g/mL, about 0.955 to 0.975 g/mL, 0.960 to about 0.985 g/mL, about 0.960 to about 0.980 g/mL, about 0.960 to 0.975 g/mL, 0.965 to about 0.985 g/mL, about 0.965 to about 0.980 g/mL, about 0.965 to 0.975 g/mL, 0.970 to about 0.985 g/mL, about 0.970 to about 0.980 g/mL, about 0.970 to 0.975 g/mL.

The alkyl 3-hydroxybutyrate can have a solubility limit in deionized water at 23° C. of at least about 2 weight percent, at least about 2.5 weight percent, at least about 3 weight percent, at least about 3.5 weight percent, at least about 3.75 weight percent and/or not more than about 20 weight percent, not more than about 15 weight percent, not more than about 10 weight percent, not more than about 5 weight percent. The solubility limit of the alkyl 3-hydroxybutyrate in deionized water at 23° C. can be in the range of from about 2 to about 20 weight percent, about 2 to about 15 weight percent, about 2 to about 10 weight percent, about 2 to about 5 weight percent, about 2.5 to about 20 weight percent, about 2.5 to about 15 weight percent, about 2.5 to about 10 weight percent, about 2.5 to about 5 weight percent, about 3 to about 20 weight percent, about 3 to about 15 weight percent, about 3 to about 10 weight percent, about 3 to about 5 weight percent, about 3.5 to about 20 weight percent, about 3.5 to about 15 weight percent, about 3.5 to about 10 weight percent, about 3.5 to about 5 weight percent, about 3.75 to about 20 weight percent, about 3.75 to about 15 weight percent, about 3.75 to about 10 weight percent, about 3.75 to about 5 weight percent.

The solubility limit of deionized water at 23° C. in the alkyl 3-hydroxybutyrate may be at least about 6 weight percent, at least about 8 weight percent, at least about 10 weight percent and/or not more than about 25 weight percent, not more than about 20 weight percent, not more than about 12 weight percent. The solubility limit of deionized water at 23° C. in the alkyl 3-hydroxybutyrate can be in the range of from about 6 to about 25 weight percent, about 6 to about 15 weight percent, about 6 to about 12 weight percent, about 8 to about 25 weight percent, about 8 to about 15 weight percent, about 8 to about 12 weight percent, about 10 to about 25 weight percent, about 10 to about 15 weight percent, about 10 to about 12 weight percent.

Additionally, the alkyl 3-hydroxybutyrate may be described by one or more of the following Hansen solubility parameters. For example, the alkyl 3-hydroxybutyrate may have a Hansen polar solubility parameter ($\sigma_p$ or "P parameter") of at least about 2.50 $(cal/cm^3)^{1/2}$, at least about 2.75 $(cal/cm^3)^{1/2}$, at least about 2.80 $(cal/cm^3)^{1/2}$, at least about 2.95 $(cal/cm^3)^{1/2}$, at least about 3.00 $(cal/cm^3)^{1/2}$, at least about 3.10 $(cal/cm^3)^{1/2}$ and/or not more than about 3.4 $(cal/cm^3)^{1/2}$, not more than about 3.30 $(cal/cm^3)^{1/2}$, not more than about 3.25 $(cal/cm^3)^{1/2}$, calculated using the "Hansen Solubility Parameters in Practice" software package $3^{rd}$ ed., version 3.1, by S. Abbott and C. Hansen.

The Hansen polar solubility parameter, which measures the permanent dipole moment and permanent dipole interactions of a molecule, can be in the range of from about 2.5 to about 3.4 $(cal/cm^3)^{1/2}$, about 2.5 to about 3.3 $(cal/cm^3)^{1/2}$, about 2.5 to about 3.25 (cal/cm$^3$)$^{1/2}$, 2.75 to about 3.4 (cal/cm$^3$)$^{1/2}$, about 2.75 to about 3.3 (cal/cm$^3$)$^{1/2}$, about 2.75 to about 3.25 (cal/cm$^3$)$^{1/2}$, 2.8 to about 3.4 (cal/cm$^3$)$^{1/2}$, about 2.8 to about 3.3 (cal/cm$^3$)$^{1/2}$, about 2.8 to about 3.25 (cal/cm$^3$)$^{1/2}$, 2.95 to about 3.4 (cal/cm$^3$)$^{1/2}$, about 2.95 to about 3.3 (cal/cm$^3$)$^{1/2}$, about 2.95 to about 3.25 (cal/cm$^3$)$^{1/2}$, 3.0 to about 3.4 (cal/cm$^3$)$^{1/2}$, about 3.0 to about 3.3 (cal/cm$^3$)$^{1/2}$, about 3.0 to about 3.25 (cal/cm$^3$)$^{1/2}$, 3.1 to about 3.4 (cal/cm$^3$)$^{1/2}$, about 3.1 to about 3.3 (cal/cm$^3$)$^{1/2}$, about 3.1 to about 3.25 (cal/cm$^3$)$^{1/2}$ for the alkyl 3-hydroxybutyrate.

The alkyl 3-hydroxybutyrate can have a Hansen hydrogen bonding solubility parameter ($\sigma_h$ or "H parameter") of at least about 5.40 (cal/cm$^3$)$^{1/2}$, at least about 5.40 (cal/cm$^3$)$^{1/2}$, at least about 5.60 (cal/cm$^3$)$^{1/2}$, at least about 5.65 (cal/cm$^3$)$^{1/2}$, at least about 5.70 (cal/cm$^3$)$^{1/2}$ and/or not more than about 6.10 (cal/cm$^3$)$^{1/2}$, not more than about 5.95 (cal/cm$^3$)$^{1/2}$, not more than about 5.90 (cal/cm$^3$)$^{1/2}$, not more than about 5.85 (cal/cm$^3$)$^{1/2}$, calculated as described above.

The Hansen hydrogen bonding solubility parameter, which measures electron exchange, can be in the range of from about 5.40 to about 6.10 (cal/cm$^3$)$^{1/2}$, about 5.40 to about 5.95 (cal/cm$^3$)$^{1/2}$, about 5.40 to about 5.90 (cal/cm$^3$)$^{1/2}$, about 5.40 to about 5.85 (cal/cm$^3$)$^{1/2}$ about 5.60 to about 6.10 (cal/cm$^3$)$^{1/2}$, about 5.60 to about 5.95 (cal/cm$^3$)$^{1/2}$, about 5.60 to about 5.90 (cal/cm$^3$)$^{1/2}$, about 5.60 to about 5.85 (cal/cm$^3$)$^{1/2}$, about 5.65 to about 6.10 (cal/cm$^3$)$^{1/2}$, about 5.65 to about 5.95 (cal/cm$^3$)$^{1/2}$, about 5.65 to about 5.90 (cal/cm$^3$)$^{1/2}$, about 5.65 to about 5.85 (cal/cm$^3$)$^{1/2}$, about 5.70 to about 6.10 (cal/cm$^3$)$^{1/2}$, about 5.70 to about 5.95 (cal/cm$^3$)$^{1/2}$, about 5.70 to about 5.90 (cal/cm$^3$)$^{1/2}$, about 5.70 to about 5.85 (cal/cm$^3$)$^{1/2}$ for the alkyl 3-hydroxybutyrate.

The alkyl 3-hydroxybutyrate can have a Hansen dispersion solubility parameter ($\sigma_d$ or "D parameter") of at least about 7.50 (cal/cm$^3$)$^{1/2}$, at least about 7.75 (cal/cm$^3$)$^{1/2}$, at least about 8.00 (cal/cm$^3$)$^{1/2}$, at least about 8.03 (cal/cm$^3$)$^{1/2}$ and/or not more than about 8.15 (cal/cm$^3$)$^{1/2}$, not more than about 8.10 (cal/cm$^3$)$^{1/2}$, not more than about 8.05 (cal/cm$^3$)$^{1/2}$, not more than about 8.00 (cal/cm$^3$)$^{1/2}$, calculated as described above.

The Hansen dispersion solubility parameter, which measures nonpolar interactions derived from atomic forces, of the alkyl 3-hydroxybutyrate can be in the range of from about 7.50 to about 8.15 (cal/cm$^3$)$^{1/2}$, about 7.50 to about 8.10 (cal/cm$^3$)$^{1/2}$, about 7.50 to about 8.05 (cal/cm$^3$)$^{1/2}$, about 7.50 to about 8.0 (cal/cm$^3$)$^{1/2}$, about 7.75 to about 8.15 (cal/cm$^3$)$^{1/2}$, about 7.75 to about 8.10 (cal/cm$^3$)$^{1/2}$, about 7.75 to about 8.05 (cal/cm$^3$)$^{1/2}$, about 7.75 to about 8.0 (cal/cm$^3$)$^{1/2}$, about 8.0 to about 8.15 (cal/cm$^3$)$^{1/2}$, about 8.0 to about 8.10 (cal/cm$^3$)$^{1/2}$, about 8.0 to about 8.05 (cal/cm$^3$)$^{1/2}$, about 8.03 to about 8.15 (cal/cm$^3$)$^{1/2}$, about 8.03 to about 8.10 (cal/cm$^3$)$^{1/2}$, about 8.03 to about 8.05 (cal/cm$^3$)$^{1/2}$.

The alkyl 3-hydroxybutyrate can have a total Hansen solubility parameter of at least about 10.1 (cal/cm$^3$)$^{1/2}$, at least about 10.2 (cal/cm$^3$)$^{1/2}$, at least about 10.25 (cal/cm$^3$)$^{1/2}$, at least about 10.3 (cal/cm$^3$)$^{1/2}$ and/or not more than about 10.5 (cal/cm$^3$)$^{1/2}$, not more than about 10.45 (cal/cm$^3$)$^{1/2}$, not more than about 10.40 (cal/cm$^3$)$^{1/2}$, calculated as described above. The total Hansen solubility parameter of the alkyl 3-hydroxybutyrate can be in the range of from about 10.1 to about 10.5 (cal/cm$^3$)$^{1/2}$, about 10.1 to about 10.45 (cal/cm$^3$)$^{1/2}$, about 10.1 to about 10.40 (cal/cm$^3$)$^{1/2}$, about 10.2 to about 10.5 (cal/cm$^3$)$^{1/2}$, about 10.2 to about 10.45 (cal/cm$^3$)$^{1/2}$, about 10.2 to about 10.40 (cal/cm$^3$)$^{1/2}$, about 10.25 to about 10.5 (cal/cm$^3$)$^{1/2}$, about 10.25 to about 10.45 (cal/cm$^3$)$^{1/2}$, about 10.25 to about 10.40 (cal/cm$^3$)$^{1/2}$, about 10.3 to about 10.5 (cal/cm$^3$)$^{1/2}$, about 10.3 to about 10.45 (cal/cm$^3$)$^{1/2}$, about 10.3 to about 10.40 (cal/cm$^3$)$^{1/2}$.

The alkyl 3-hydroxybutyrate can have a surface tension, measured using the ring pull method with a Krüss K100 tensiometer, of at least about 24.5 dynes/cm, at least about 25.0 dynes/cm, at least about 25.5 dynes/cm, and/or not more than about 30 dynes/cm, not more than about 29 dynes/cm, not more than about 28 dynes/cm, not more than about 27 dynes/cm, not more than about 26.5 dynes/cm. The surface tension of the alkyl 3-hydroxybutyrate can be in the range of from about 24.5 to about 30 dynes/cm, about 24.5 to about 29 dynes/cm, about 24.5 to about 28 dynes/com, about 24.5 to about 27 dynes/cm, about 24.5 to about 26.5 dynes/cm, about 25 to about 30 dynes/cm, about 25 to about 29 dynes/cm, about 25 to about 28 dynes/com, about 25 to about 27 dynes/cm, about 25 to about 26.5 dynes/cm, about 25.5 to about 30 dynes/cm, about 25.5 to about 29 dynes/cm, about 25.5 to about 28 dynes/com, about 25.5 to about 27 dynes/cm, about 25.5 to about 26.5 dynes/cm.

The alkyl 3-hydroxybutyrate may also have the ability to bring together and homogenize two immiscible liquids, for example, an oil and water. This ability is called "coupling efficiency" and can be measured by adding the alkyl 3-hydroxybutyrate to 1.0 gram of an oil and 1.0 gram of deionized water with vigorous stirring or shaking until the mixture becomes clear. The result can then be expressed as the number of grams of solvent divided by the total grams of oil and water. The alkyl 3-hydroxybutyrate can have a corn oil-water coupling efficiency measured at 23° C. of at least about 5 grams of alkyl 3-hydroxybutyrate per total grams of oil and water (g/g), at least about 6 g/g, at least about 7 g/g and/or not more than about 15 g/g, not more than about 12 g/g, or not more than about 10 g/g. The alkyl 3-hydroxybutyrate may also have a corn oil-water coupling efficiency in the range of from about 5 to about 15 g/g, about 5 to about 12 g/g, about 5 to about 10 g/g, about 6 to about 15 g/g, about 6 to about 12/g/g, about 6 to about 10 g/g, about 7 to about 15 g/g, about 7 to about 12 g/g, about 7 to about 10 g/g.

The alkyl 3-hydroxybutyrate prepared according to a method of the present invention may be suitable for use in a variety of end applications. For example, the alkyl 3-hydroxybutyrate produced as described herein may be used as a solvent in an aqueous cleaning composition. Such cleaning compositions, which may further include water and an optional surfactant and/or additive, may effectively remove different types of soil from a variety of substrates, including, for example, those including hard surfaces made of metal, glass, plastic, ceramic, porcelain, fiberglass, stone, concrete, plaster, brick, marble, vinyl, natural or composite wood, wall board, or combinations thereof. Such cleaning compositions may take many forms, including solutions, gels, emulsions, foams, aerosols, pastes, and/or slurries and may be used as or in descaling compositions, a bathroom cleaners, a glass cleaners, a floor cleaners, a biocidal cleaners, an automotive cleaners, a wood cleaners, a plastic cleaners, a paint strippers, a degreasing compositions, a desoiling compositions, and/or an all-purpose general cleaners used on floors, walls, tiles, windows, sinks, showers, bathtubs, shower curtains, wash basins, drains, dishes, fixtures, fittings, counter tops, cabinets, stove tops, appliance surfaces, such as internal and external surfaces of refrigerators, microwave ovens, convection ovens, freezers, dishwashers, washing machines, and dryers.

The following examples are intended to be illustrative of the present invention in order to teach one of ordinary skill in the art to make and use the invention and are not intended to limit the scope of the invention in any way.

EXAMPLES

Example 1

Synthesis of n-Butyl Acetoacetate from Diketene

A charge of 5,600 grams of n-butanol was placed in a 22 L, jacketed reaction flask equipped with an overhead stirrer, reflux condenser, thermocouple, and a liquid feed pump. A glycol-water mixture maintained at a set temperature of 70° C. was circulated through the reactor jacket from a bath reservoir to bring the reactor contents to 50° C. When the reactor reached 50° C., 365 mL of triethylamine was added. Diketene, in an amount of 6,049 grams, was then added at a rate of 15 mL/min. The reactor temperature was increased slowly during the addition of diketene. When the reactor reached 55° C., the circulating liquid bath temperature was lowered to cool the reactor and to maintain the reaction temperature in the range of from about 55 to about 57° C. The addition of the entire charge of diketene, (4.1 kg) required 8 hours. The reaction mixture was then allowed to cool slowly to 35° C. with continued agitation. The crude reaction product was then purified by fractional distillation at a pressure of 6 torr and provided pure n-butyl acetoacetate as a clear, colorless liquid.

Example 2

Synthesis of Butyl 3-Hydroxybutyrate from n-Butyl Acetoacetate

A charge of 150 g of n-butyl acetoacetate, prepared as described in Example 1 above, and 4.5 g of a 5 percent ruthenium-on-carbon catalyst (as a water wet solid, 50 percent solids) were sealed in a 300 mL high-pressure autoclave and were pressurized to 55.2 bars gauge (800 psig) with hydrogen. The reactor contents were heated to 65° C. with stirring over a period of 20 min and allowed to stir at this temperature until hydrogen uptake ceased (1.25 h). The reactor was then allowed to cool to room temperature and the reaction mixture was filtered through a pad of diatomaceous earth to remove the catalyst. A light yellow crude solution was obtained that contained n-butyl 3-hydroxybutyrate as well as trace amounts of water and the ester dimer (4-butoxy-4-oxobutan-2-yl 3-hydroxybutyrate), as determined by gas chromatographic analysis. Fractional distillation of the crude n-butyl 3-hydroxybutyrate solution at a pressure of 6 torr produced pure n-butyl 3-hydroxybutyrate as a colorless liquid.

Example 3

Prophetic

Synthesis of Butyl 3-Hydroxybutyrate from Diketene

This prophetic example relates to the production of n-butyl 3-hydroxybutyrate by reacting diketene with n-butanol and the hydrogenating the resulting n-butyl acetoacetate to form n-butyl 3-hydroxybutyrate. This prophetic example is described with respect to the schematic process flow diagrams provided in FIGS. 1 and 2.

A stream of n-butanol in line 20 is added to a reaction vessel (not shown) disposed within reaction zone 14 of production facility 10. The n-butanol (n-BuOH) is combined with a stream of triethylamine (TEA) catalyst introduced into reaction zone 14 via line 22. The mass flow rate of the n-butanol, which has a minimum purity of 99.8 weight percent, is approximately 27,400 kg/day. The triethylamine is added to the reaction mixture to achieve a 5 weight percent loading, based on the total weight of the reaction mixture. The contents of the reaction vessel are stirred and a stream of diketene, optionally purified from a stream of crude diketene in an upstream purification zone 12, is added to the reaction vessel via line 24 at a mass flow rate of approximately 27,700 kg/day. During the addition of diketene, the contents of the heat-jacketed reaction vessel are maintained at a temperature between about 75° C. and about 92° C.

The reaction product stream, which contains the n-butyl acetoacetate (nBAA) intermediate formed by the reaction of diketene and n-butanol, is withdrawn from reaction zone 14 via line 26. The stream is then introduced into a separation zone 16, wherein the reaction byproducts and other impurities are separated from the n-butyl acetoacetate using a two-column distillation system as shown in FIG. 2. First distillation column 110, which operates at a top temperature between about 30° C. and about 50° C. and an overhead pressure of about 15 torr, separates a variety of low-boiling components, including acetone, n-butanol, and butyl acetate, in an overhead stream withdrawn from first distillation column 110 via line 28. The bottoms stream withdrawn from first distillation column 110 in line 130 is routed to a second distillation column 120, which operates at a top temperature between about 80° C. and about 82° C. and a top pressure of about 10 torr. Second distillation column 120 removes higher-boiling components, including the dimer 4-butoxy-4-oxobutan-2-yl 3-hydroxybutyrate, as a bottoms stream in line 30. The n-butyl acetoacetate-enriched overhead stream withdrawn from the second distillation column 120 via line 32 is routed to a hydrogenation zone 18, as shown in FIG. 1.

In hydrogenation zone 18, the stream in line 32 exiting separation zone 16 is contacted with a hydrogen-containing gas introduced into hydrogenation zone 18 via line 34. The hydrogen-containing gas includes 99 volume percent hydrogen, with the balance being trace amounts of methane (not more than 1 volume percent), nitrogen (not more than 0.5 volume percent), carbon monoxide (not more than 30 ppm) and sulfur (not more than 0.1 ppm). The contacting is carried out in the presence of 70 kg of a hydrogenation catalyst comprising 5 weight percent ruthenium on a carbon support. During hydrogenation, the temperature is maintained at about 80° C. and the pressure is kept between 800 psig and 1000 psig. Hydrogenation is carried out for approximately 3 hours. The resulting crude product stream withdrawn from hydrogenation zone via line 36 is filtered in a purification zone 20 to provide the final n-butyl 3-hydroxybutyrate product stream in line 38. Compositions of select streams shown in FIGS. 1 and 2 are provided in Table 2, below.

TABLE 2

Compositions of Select Streams in 3-Hydroxybutyrate Production Facility 10 in FIG. 1

| Component | Stream 26 | Stream 28 | Stream 32 | Stream 36 |
|---|---|---|---|---|
| nBuOH (wt %) | 5-7 | 32-38 | <0.5 | <0.80 |
| nBAA (wt %) | 75-85 | 12-18 | 98-100 | <0.1 |
| NBHB (wt %) | — | — | — | 95-99 |
| TEA (wt %) | 1-3 | 5-10 | <0.1 | — |
| Diketene (wt %) | 1-3 | — | — | — |
| High boilers (wt %) | 5-7 | — | — | — |
| Acetic acid (wt %) | — | <1 | <0.2 | — |
| Acetone (wt %) | — | 10-15 | <1 | — |

TABLE 2-continued

Compositions of Select Streams in 3-Hydroxybutyrate Production Facility 10 in FIG. 1

| Component | Stream | | | |
|---|---|---|---|---|
| | 26 | 28 | 32 | 36 |
| Butyl acetate (wt %) | — | 20-30 | 1-2 | — |
| 4-butoxy-4-oxobutan-2-yl 3-hydroxybutyrate (wt %) | — | — | — | 0.1-0.8 |
| Water (wt %) | — | — | — | 0.5-1 |

The preferred forms of the invention described above are to be used as illustration only, and should not be used in a limiting sense to interpret the scope of the present invention. Obvious modifications to the exemplary one embodiment, set forth above, could be readily made by those skilled in the art without departing from the spirit of the present invention.

The inventors hereby state their intent to rely on the Doctrine of Equivalents to determine and assess the reasonably fair scope of the present invention as pertains to any apparatus not materially departing from but outside the literal scope of the invention as set forth in the following claims.

We claim:

1. A method of making an alkyl 3-hydroxybutyrate, said method comprising:
    (a) reacting an alkyl alcohol with diketene to provide a first reaction mixture comprising an alkyl acetoacetate; and
    (b) hydrogenating at least a portion of said alkyl acetoacetate in said first reaction mixture to thereby provide a hydrogenated product stream comprising alkyl 3-hydroxybutyrate,
    wherein said alkyl group on the alkyl 3-hydroxybutyrate comprises an isopropyl group, n-propyl group, isobutyl group, n-butyl group, 2-butyl (sec-butyl) group, 2,2-dimethylethyl (tert-butyl) group, 3,3-dimethylpentyl (isopentyl) group, 1-pentyl (n-pentyl) group, 1-methylbutyl(2-pentyl) group, 2-methylbutyl group, 2-ethylpropyl(3-pentyl) group, 1,1-dimethylpropyl group, 1,2-dimethylpropyl group, 2,2-dimethylpropyl (neopentyl) group, or a cyclopentyl group,
    wherein said hydrogenating includes contacting at least a portion of said first reaction mixture with a hydrogen-containing gas and then heating the resulting mixture to a hydrogenation temperature in the range of from about 70° C. to about 90° C., in the presence of a hydrogenation catalyst.

2. The method of claim 1, wherein the alkyl group of said alkyl 3-hydroxybutyrate is an isopropyl group.

3. The method of claim 1, wherein the alkyl group of said alkyl 3-hydroxybutyrate is selected from the group consisting of isobutyl, n-butyl, and 2-butyl.

4. The method of claim 1, wherein at least a portion of said reacting is carried out in the presence of a catalyst.

5. The method of claim 4, wherein said catalyst has a vapor pressure in the range of from about 45 torr to about 75 torr measured at 25° C.

6. The method of claim 4, wherein said catalyst is present in an amount in the range of from about 0.1 to about 10 weight percent, based on the total weight of said reaction mixture.

7. The method of claim 4, wherein said catalyst comprises a trialkylamine.

8. The method of claim 1, wherein said alkyl alcohol is reacted with said diketene at a temperature in the range of from about 55 to about 105° C.

9. The method of claim 1, wherein said alkyl alcohol is reacted with said diketene at a pressure within a range of 13 to 25 psia.

10. The method of claim 1, further comprising, prior to said reacting, combining a catalyst with said alkyl alcohol to form a precursor reaction mixture and adding said diketene to said precursor reaction mixture to initiate said reacting, wherein during the addition of said diketene to said precursor reaction mixture, the average temperature of said precursor reaction mixture is maintained at a target temperature in the range of from about 65 to about 105° C.

11. The method of claim 1, further comprising prior to said hydrogenating, separating at least one impurity from said first reaction mixture to provide a purified reaction mixture and hydrogenating at least a portion of said purified reaction mixture.

12. The method of claim 11, wherein at least a portion of said separating is carried out at a pressure not more than 760 torr.

13. The method of claim 12, wherein at least a portion of said separating is carried out at a temperature in the range of from about 15 to about 70° C. and a pressure in the range of from about 1 to about 30 torr.

14. The method of claim 13, wherein another portion of said separating is carried out at a temperature in the range of from about 70 to about 90° C. and a pressure in the range of from about 1 to about 15 torr.

15. The method of claim 11, wherein said impurity comprises a component selected from the group consisting of acetic acid, acetone, alkyl acetate, and combinations thereof.

16. The method of claim 11, wherein said impurity comprises a component selected from the group consisting of dimers of acetoacetate, alkyl butyrate, and combinations thereof.

17. The method of claim 1, wherein the first reaction mixture is contacted with a hydrogen-containing gas at a pressure in the range of from about 300 psig to about 1200 psig.

18. The method of claim 1, wherein the first reaction mixture has a pH in the range of from about 4 to about 8 upon contact with the hydrogen containing gas.

19. The method of claim 1, wherein said hydrogenation catalyst comprises at least one catalytic metal selected from the group consisting of platinum, palladium, ruthenium, nickel, and combinations thereof.

20. The method of claim 19, wherein said hydrogenation catalyst is a heterogeneous catalyst, wherein said catalytic metal is supported on, in, and/or within a support, and wherein said support is not acidic.

21. The method of claim 19, wherein said catalytic metal is selected from the group consisting of ruthenium, nickel, and combinations thereof.

22. The method of claim 20, wherein said catalytic metal is present in said catalyst in an amount in the range of from about 1 to about 6 weight percent, based on the total weight of said catalyst.

23. The method of claim 22, wherein said catalytic metal is ruthenium.

24. The method of claim 1, wherein said alkyl 3-hydroxybutyrate has a vapor pressure in the range of from about 0.055 to about 0.10 torr measured at 20° C.

25. The method of claim 1, wherein said alkyl 3-hydroxybutyrate has a corn oil-water coupling efficiency measured at 23° C. in the range of from 5 grams/gram to 12 grams/gram.

26. The method of claim 1, wherein at least a portion of said reacting and at least a portion of said hydrogenating are carried out in different vessels.

27. The method of claim 1, wherein at least one of said reacting and said hydrogenating are carried out continuously.

28. A method for producing an alkyl 3-hydroxybutyrate, said method comprising:
(a) separating a feed stream comprising at least one alkyl acetoacetate in a first distillation column into an impurities-enriched overhead vapor stream and an impurities-depleted liquid bottoms stream,
(b) separating said impurities-depleted liquid bottoms stream into an alkyl acetoacetate-enriched overhead vapor stream and an alkyl acetoacetate-depleted liquid bottoms stream; and
(b) hydrogenating at least a portion of the alkyl acetoacetate in said alkyl acetoacetate-enriched overhead vapor stream to thereby provide a hydrogenated product stream comprising an alkyl 3-hydroxybutyrate,
wherein said alkyl group on the alkyl 3-hydroxybutyrate comprises an isopropyl group, n-propyl group, isobutyl group, n-butyl group, 2-butyl (sec-butyl) group, 2,2-dimethylethyl (tert-butyl) group, 3,3-dimethylpentyl (isopentyl) group, 1-pentyl (n-pentyl) group, 1-methylbutyl(2-pentyl) group, 2-methylbutyl group, 2-ethylpropyl(3-pentyl) group, 1,1-dimethylpropyl group, 1,2-dimethylpropyl group, 2,2-dimethylpropyl (neopentyl) group, or a cyclopentyl group,
wherein said hydrogenating includes contacting at least a portion of said alkyl acetoacetate-enriched overhead vapor stream with a hydrogen-containing gas and then heating the resulting mixture to a hydrogenation temperature of greater than 65° C. in the presence of a hydrogenation catalyst.

29. The method of claim 28, wherein the alkyl group of said alkyl 3-hydroxybutyrate is an isopropyl group.

30. The method of claim 28, wherein the alkyl group of said alkyl 3-hydroxybutyrate is selected from the group consisting of isopropyl, isobutyl, n-butyl, and 2-butyl.

31. The method of claim 28, wherein said alkyl group of said alkyl 3-hydroxybutyrate is n-butyl.

32. The method of claim 28, wherein said impurities-depleted liquid bottoms stream comprises at least 50 percent of the total amount of alkyl acetoacetate present in said feed stream.

33. The method of claim 28, wherein the first distillation column is operated at a temperature in the range of from about 15 to about 70° C. and a pressure in the range of from about 1 to about 30 torr, wherein the molar ratio of the amount of acetoacetate in said impurities-enriched overhead vapor stream to the amount of acetoacetate in said impurities-depleted liquid bottoms stream is in the range of from about 0.01:1 to about 0.25:1.

34. The method of claim 28, wherein said impurities-depleted liquid bottoms stream comprises at least about 75 percent of the total amount of alkyl acetoacetate present in said feed stream introduced into said first distillation column.

35. The method of claim 28, wherein said impurities-enriched overhead vapor stream comprises one or more impurities selected from the group consisting of acetic acid, acetone, an alkyl alcohol, an alkyl acetate, and combinations thereof.

36. The method of claim 28, further comprising, separating at least a portion of said impurities-depleted liquid bottoms stream into an alkyl acetoacetate-enriched overhead vapor stream and an alkyl acetoacetate-depleted liquid bottoms stream in a second distillation column, wherein said impurities-depleted stream contacted with said hydrogen-containing gas comprises said second overhead stream.

37. The method of claim 36, wherein said alkyl acetoacetate-enriched overhead vapor stream has a total impurities content of not more than 1 weight percent, based on the total weight of said alkyl acetoacetate-enriched overhead vapor stream.

38. The method of claim 36, wherein at least one of said first and said second distillation columns are operated at a pressure of not more than 30 torr.

39. The method of claim 28, wherein said alkyl 3-hydroxybutyrate has a boiling point in the range of from about 210° C. to about 230° C.

40. The method of claim 28, wherein said alkyl 3-hydroxybutyrate has a vapor pressure in the range of from about 0.055 torr to about 0.10 torr measured at 20° C.

41. The method of claim 28, wherein said alkyl 3-hydroxybutyrate has a solubility in deionized water at 23° C. in the range of from about 2 to about 20 percent.

42. The method of claim 28, wherein said alkyl 3-hydroxybutyrate has a corn oil-water coupling efficiency in the range of from about 5 grams/gram to about 15 grams/gram.

43. The method of claim 28, further comprising, prior to said separating, reacting an alkyl alcohol with diketene to form a first reaction mixture comprising said alkyl acetoacetate, wherein said feed stream comprises said first reaction mixture.

44. The method of claim 1, wherein said hydrogenation temperature is in the range of from 80° C. to 90° C.

45. The method of claim 28, wherein said hydrogenation temperature is in the range of from 80° C. to 100° C.

46. The method of claim 28, wherein said hydrogenation temperature is in the range of from 70° C. to 90° C.

47. The method of claim 28, wherein said hydrogenation catalyst comprises at least one catalytic metal selected from the group consisting of ruthenium, nickel, and combinations thereof.

48. The method of claim 47, wherein said hydrogenation catalyst further comprises at least one support, wherein said support comprises carbon.

* * * * *